(12) United States Patent
Rule et al.

(10) Patent No.: US 11,020,567 B2
(45) Date of Patent: Jun. 1, 2021

(54) MEDICAL ARTICLE SECUREMENT DEVICE COMPRISING A VISCOELASTIC POLYMER

(71) Applicant: 3M INNOVATIVE PROPERTIES COMPANY, Saint Paul, MN (US)

(72) Inventors: Joseph D. Rule, Woodbury, MN (US); Jennifer N. Hanson, Woodbury, MN (US); Done Demirgoz, Saint Paul, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 0 days.

(21) Appl. No.: 16/613,863

(22) PCT Filed: May 15, 2018

(86) PCT No.: PCT/IB2018/053386
§ 371 (c)(1),
(2) Date: Nov. 15, 2019

(87) PCT Pub. No.: WO2018/211416
PCT Pub. Date: Nov. 22, 2018

(65) Prior Publication Data
US 2020/0406011 A1    Dec. 31, 2020

Related U.S. Application Data

(60) Provisional application No. 62/508,497, filed on May 19, 2017.

(51) Int. Cl.
*A61M 5/32* (2006.01)
*A61M 25/02* (2006.01)
(Continued)

(52) U.S. Cl.
CPC ............... *A61M 25/02* (2013.01); *B32B 7/12* (2013.01); *B32B 27/06* (2013.01); *A61M 2025/0266* (2013.01); *B32B 2405/00* (2013.01)

(58) Field of Classification Search
CPC ........ A61M 25/02; B32B 27/06; B32B 27/28; B32B 27/30; B32B 27/304; B32B 27/308;
(Continued)

(56) References Cited

U.S. PATENT DOCUMENTS

| RE24,906 E | 12/1960 | Ulrich |
|---|---|---|
| 3,389,827 A | 6/1968 | Abere |

(Continued)

FOREIGN PATENT DOCUMENTS

| WO | WO 01/12116 | 2/2001 |
|---|---|---|
| WO | WO 2006/065410 | 6/2006 |

(Continued)

OTHER PUBLICATIONS

Hal F. Brinson and Catherine L. Brinson, *Polymer Engineering Science and Viscoelasticity: An Introduction*, Second Edition, Springer Science and Business Media, New York, 2015.

(Continued)

*Primary Examiner* — Zachary M Davis
(74) *Attorney, Agent, or Firm* — 3M Innovative Properties Company; Trisha D. Adamson (57) ABSTRACT

Medical article securement systems comprising a viscoelastic polymer and optionally a base layer for securing a medical article to the body of a patient, and particularly, for securing various catheter systems, tubes, or other elongated medical devices to the body of a patient and methods of making and using such.

14 Claims, 3 Drawing Sheets

(51) Int. Cl.
*B32B 7/12* (2006.01)
*B32B 27/06* (2006.01)

(58) Field of Classification Search
CPC ......... B32B 27/34; B32B 27/36; B32B 27/40; C09J 2475/00; C09J 2475/006
See application file for complete search history.

(56) References Cited

U.S. PATENT DOCUMENTS

| | | | |
|---|---|---|---|
| 4,112,213 | A | 9/1978 | Waldman |
| 4,310,509 | A | 1/1982 | Berglund |
| 4,323,557 | A | 4/1982 | Rosso |
| 4,737,410 | A | 4/1988 | Kantner |
| 4,941,882 | A | 7/1990 | Ward |
| 5,131,412 | A | 7/1992 | Rankin |
| 5,135,786 | A | 8/1992 | Hayashi |
| 2009/0270825 | A1 | 10/2009 | Wciorka |
| 2010/0137775 | A1 | 6/2010 | Hu |
| 2011/0117364 | A1 | 5/2011 | Uesugi |
| 2012/0156456 | A1 | 6/2012 | Niimi |
| 2015/0025436 | A1 | 1/2015 | Tang |
| 2015/0090255 | A1 | 4/2015 | Gulliver |
| 2015/0141949 | A1 | 5/2015 | Decabooter |
| 2018/0291141 | A1* | 10/2018 | Yang .................... C08G 18/222 |

FOREIGN PATENT DOCUMENTS

| | | | |
|---|---|---|---|
| WO | WO 2012/050691 | 4/2012 | |
| WO | WO 2013/162680 | 10/2013 | |
| WO | WO 2013/181118 | 12/2013 | |
| WO | WO 2014/099709 | 6/2014 | |
| WO | WO-2015094792 A1 * | 6/2015 | ....... A61F 13/00029 |
| WO | WO 2015/124669 | 8/2015 | |
| WO | WO 2016/106207 | 6/2016 | |

OTHER PUBLICATIONS

China National Intellectual Property Administration Search Report for CN201880033093.4.
International Search Report for PCT/IB2018/053386 dated Sep. 19, 2018.
Supplementary European Search Report for EP18801835 dated Feb. 25, 2021.

* cited by examiner

MEDICAL ARTICLE SECUREMENT DEVICE COMPRISING A VISCOELASTIC POLYMER

CROSS REFERENCE TO RELATED APPLICATIONS

This application is a national stage filing under 35 U.S.C. 371 of PCT/IB2018/053386, filed May 15, 2018, which claims the benefit of U.S. Provisional Application No. 62/508,497, filed May 19, 2017, the disclosures of which are incorporated by reference in their entirety herein.

TECHNICAL FIELD

The present disclosure generally relates to medical article securement systems comprising a viscoelastic polymer for securing a medical article to the body of a patient, and particularly, for securing various catheter systems, tubes, or other elongated devices to the body of a patient.

BACKGROUND

In the course of various medical treatments, it may be necessary to introduce fluids and/or liquid medications directly into a blood vessel of a patient. A simple peripheral intravenous ("IV") catheter can be acceptable for short-term general use. These peripheral intravenous catheters are typically inserted into the lower arm and secured with tape or a simple transparent dressing. Catheters for longer-term treatment plans, often inserted centrally in the body, are commonly secured with more sophisticated means, such as a molded plastic device that is adhered to the skin.

In order to keep the catheter or other medical line properly positioned for the duration of treatment, the catheter may be secured to the patient in a variety of ways. For example, sutures may be used to attach a catheter to a patient. With sutures, the catheter is stitched onto the skin. Sutures, however, can be a source of infection, can cause pain and inflammation, and can make it more difficult to clean around the incision site. Sutures also require time and skill to place, and can cause scarring. Other securement systems often employ a rigid component, such as, for example, a clip or an injection-molded clamp, that is coupled to a conformable, adhesive-coated backing to hold the rigid component on the patient's skin. This rigidity gives positive securement to the catheter tubing, but the cost of such securement systems may prohibit their use in some markets.

A common, low-cost method of securing a catheter is by taping the catheter or medical line to the patient's skin. However, securement force provided by taping tends to be lower and more inconsistent as compared to other means of securement and typically needs to be removed and replaced often.

SUMMARY

The present disclosure is generally directed to medical article securement systems and methods, and particularly, medical article securement systems and methods that are adapted to accommodate and reliably secure medical articles, particularly elongated medical articles. The medical article securement systems and methods of the present disclosure are generally easy to use and are designed to incorporate the benefits of a rigid component with conformability in order to reliably retain a medical article, e.g., a catheter or medical line, on a patient for a desired treatment period. One aspect of the present disclosure provides securement device including a polymer film having a first major surface and a second major surface opposite the first major surface, the polymer film having a thickness of at least 0.1 mm, a glass transition temperature, Tg, of at least 15° C. and no greater than 45° C., a tan δ max of at least 0.4, and a tensile storage modulus E' of at least 10 MPa at 30° C., 1 Hz when tested according to Dynamic Mechanical Analysis, and an adhesive on the second major surface of the polymer film. The device can further include a base layer.

In another aspect, provided is a medical tubing securement device including a polymer film having a first major surface, a second major surface opposite the first major surface, a formed bend, the bend defining a channel dimensioned to receive at least a portion of a medical tubing, and a notch formed through the polymer film adjacent the bend, such that the notch is aligned with the channel, and an adhesive on the second major surface of the polymer film. The device can further include a base layer.

Other features and advantages of the present disclosure will be further understood upon consideration of the detailed description as well as the appended claims.

Repeated use of reference characters in the specification and drawings is intended to represent the same or analogous features or elements of the disclosure. It should be understood that numerous other modifications and embodiments can be devised by those skilled in the art, which fall within the scope and spirit of the principles of the disclosure. The figures may not be drawn to scale.

DETAILED DESCRIPTION

It is desirable to provide healthcare professionals with the performance of medical device securement systems that employ a rigid component for improved securement, but also maintain the simplicity and low cost of a tape securement method. As disclosed herein, medical article securement systems comprising a viscoelastic polymer of the present disclosure can provide the benefits of a securement system employing a rigid component, e.g., rigidity when force is applied, in addition to the benefits of tape securement, e.g. conformability, as the securement system may be formed about the contours of a medical device. On relatively long time scales, such as the minutes and hours during which a device of the present disclosure rests against a patient's skin, the viscoelastic polymer layer may act as a soft, conformable backing, allowing for wetting out the adhesive and minimizing edge lift. However, on relatively short time scales, such as the fraction of a second in which an accidental tug is applied to tubing, the same viscoelastic polymer layer may behave rigidly to help prevent the initiation of a peel front that could allow the medical securement device to debond from the skin.

The terms "longitudinal" and "axial" are used to refer to a direction or axis that is generally parallel to the direction in which the medical article extends and generally parallel to the overall direction of fluid flow, e.g., along a catheter line.

The term "lateral" is used to refer to a direction or axis that is perpendicular to the longitudinal axis or direction and is used to represent side-to-side motion of a medical article.

The terms "vertical" and "normal" are used to refer to a direction or axis that is normal to both the longitudinal and lateral directions or axes, as well as to the surface of a patient's skin when the medical article securement system is coupled to the patient's skin, and is used to represent the direction of motion toward and away from the skin surface.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof are used broadly and encompass both direct and indirect couplings. It is to be understood that other embodiments may be utilized, and structural or logical changes may be made without departing from the scope of the present disclosure. Furthermore, terms such as "front," "rear," "top," "bottom," and the like are only used to describe elements as they relate to one another, but are in no way meant to recite specific orientations of the apparatus, to indicate or imply necessary or required orientations of the apparatus, or to specify how the invention described herein will be used, mounted, displayed, or positioned in use.

The present disclosure generally relates to medical article securement systems comprising a viscoelastic polymer and methods for safely and reliably securing a medical article upon a desired location of a patient's body.

Examples of medical articles that can be employed with the medical article securement system of the present disclosure include, but are not limited to, connector fittings, catheter systems (e.g., including catheters, catheter hubs, catheter adaptors), fluid supply lines, drainage tubes, other similar articles, or combinations thereof. Examples of catheter systems can include, but are not limited to, peripheral intravenous ("PIV") catheters, central venous catheters ("CVCs"), peripherally inserted central catheters ("PICCs"), arterial catheters, urinary catheters, and dialysis catheters.

Polymer Films

Polymer films useful in embodiments of the present application may include viscoelastic polymers. The term "viscoelastic polymer," as used herein refers to a solid polymer showing a combination of both elastic and viscous behaviors. Methods of making and analyzing such polymer films are known in the art and are described, for example, in Hal F. Brinson and Catherine L. Brinson, *Polymer Engineering Science and Viscoelasticity: An Introduction*, Second Edition, Springer Science and Business Media, New York, 2015. Polymer films useful in embodiments of the present disclosure may comprise a polymer selected from the group consisting of a polyurethane, a polyvinyl chloride, an acrylic, a polyester, a polyamide, and combinations thereof. In some embodiments, the polymer film may comprise a polyurethane selected from the group consisting of an ester-based aliphatic polyurethane, an ether-based aliphatic polyurethane, an ester-based aromatic polyurethane, an ether-based aromatic polyurethane, a polycarbonate-based polyurethane, and combinations thereof. In some embodiments, the polymer film may comprise a thermoplastic polyurethane.

In embodiments of the present disclosure, the polymer film must be thick enough to resist undesirable deformation and tearing, but not so thick that the polymer film does not readily conform to the contours of the medical article to be attached to the patient or to the patient's skin. In addition, the polymer film should be thin enough to allow for some level of moisture vapor transmission. In some embodiments, the polymer film may have a thickness of at least 0.1 mm, at least 0.13 mm, at least 0.15 mm, at least 0.2 mm, at least 0.3 mm, or at least 0.5 mm. In some embodiments, the thickness of the backing may be no greater than 1 mm, no greater than 0.9 mm, no greater than 0.8 mm, no greater than 0.75 mm, no greater than 0.7 mm, or no greater than 0.6 mm. In some embodiments, the polymer film may have a thickness of about 0.1 mm to about 1 mm, about 0.13 mm to about 0.9 mm, or about 0.15 mm to about 0.8 mm.

The glass transition temperature ("Tg") of a polymer is the temperature, or temperature range, at which a polymer softens from a hard, glassy material to a soft, rubbery material. The glass transition temperature, Tg, of a polymer film useful in embodiments of the present disclosure is at least 15° C., at least 20° C., at least 22° C., at least 23° C., at least 25° C., at least 30° C., or at least 34° C. In some embodiments, the glass transition temperature, Tg, is no greater than 45° C., no greater than 44° C., no greater than 43° C., no greater than 42° C., or no greater than 41° C. In some embodiments, the glass transition temperature, Tg, is about 15° C. to about 45° C., about 15° C. to about 44° C., about 15° C. to about 43° C., about 15° C. to about 42° C., or about 15° C. to about 41° C.

As used in the present disclosure, Tg also refers to the temperature at which energy dissipation (as indicated by the tan delta ("tan δ") value) in a Dynamic Mechanical Analysis ("DMA") test reaches a relative maximum. Tan δ is the ratio of loss modulus over the storage modulus, so higher values of the tan δ signal indicate that the energy used to deform the polymer film sample in the DMA test is lost to greater degree rather than being elastically returned to the system. Therefore, high tan δ signals may also correspond to higher capacity for energy dissipation as a material is deformed. While not wishing to be bound by a particular theory, it is believed that this energy dissipation is significant in polymer films of the present disclosure because energy may be dissipated by deforming the viscoelastic polymer film and is therefore not transferred as effectively to the adhesive. Thus the adhesive bond is relatively protected compared to a non-viscoelastic film that does not dissipate energy as it is deformed, resulting in better adhesion of the medical article securement to the patient. Polymer films useful in embodiments of the present disclosure have a tan δ max of at least 0.4, of at least 0.5, of at least 0.6, or of at least 0.7. In some embodiments, polymer films of the present disclosure have a tan δ max no greater than 2.0, no greater than 1.9, no greater than 1.8, or no greater than 1.7. In some embodiments, polymer films of the present disclosure have a tan δ max of 0.4 to 2.0, 0.5 to 1.9, or 0.6 to 1.8.

Tensile storage modulus ("E'") is a measure of the stiffness of a material as it is deformed in the DMA test. The E' of a polymer film at 30° C. is of particular interest if the polymer will be used in close proximity to human skin (the normal temperature of human skin is around 30° C.). If the E' value of a polymer film is too low at use temperature (i.e., at about 30° C.), then the material will be very flexible or stretchy and may be unsuitable for use in embodiments of the present disclosure, as very flexible polymer film may deform too easily and allow the polymer film and adhesive to peel off of the test substrate. Conversely, if the E' value of a polymer film is too high at use temperature, then the material may conform poorly to the patient and/or medical article. Polymer films suitable for use in embodiments of the present disclosure may have a tensile storage modulus E' of at least 10 MPa, at least 20 MPa, at least 30, MPa, at least 40 MPa, or at least 50 MPa at 30° C., 1 Hz when tested according to Dynamic Mechanical Analysis. Polymer films suitable for use in embodiments of the present disclosure may have a tensile storage modulus E' of no greater than 2,000 MPa, no greater than 1,900 MPa, no greater than 1,800 MPa, no greater than 1,700 MPa, or no greater than 1,600 MPa at 30° C., 1 Hz when tested according to Dynamic Mechanical Analysis. In some embodiments, polymer films suitable for use in embodiments of the present disclosure may have a tensile storage modulus E' of about 10 MPa to about 2,000 MPa, about 20 MPa to about 1,800 MPa, or about 30 MPa to about 1,600 MPa.

In some embodiments, the polymer film may have a smooth texture. In other embodiments, the polymer film may have a patterned texture resulting from a surface modification and/or perforation. Though not wishing to be bound to a particular theory, it is believed that in some applications surface modifications and/or perforations on the polymer film may result in a securement device with desirable handling and use characteristics, e.g., ease of manipulation about a medical device, because the surface modifications and/or perforations may allow for collection and/or release of moisture and lead to a softening of the securement device where it contacts the patient's skin. The surface modification and or perforation of the polymer film may be accomplished by embossing or by other methods known to those of skill in the art. The surface modification and/or perforation may comprise a regular pattern and/or random pattern of dots, lines (e.g., straight lines, wavy lines) or shapes, regular or irregular, such as for example, polygons (e.g., squares, rectangles, triangles, hexagons), circles, ellipses, stars, crescents, and the like, or combinations thereof. In some embodiments, surface modification of the polymer film may be provided by use of an embossing tool comprising a plate with an array of machined posts, each post 0.6 mm tall with a square base 0.2 mm×0.2 mm and a square tip 0.1 mm×0.1 mm, positioned in an array having square packing and a pitch of 0.3 mm.

In some embodiments, the polymer film may have a formed shape such as, for example, a bend defining a channel dimensioned to receive at least a portion of a medical article for securement. In some embodiments, the bend may be formed by heating the polymer film in an oven at about 125° C. for about 30 minutes followed by cooling to room temperature while the film is positioned over a rod (e.g., a wooden or metal cylinder) having a desired radius to provide a polymer film comprising a channel with the desired radius. In some embodiments, the desired radius of the bend may be at least 0.5 mm, at least 1 mm, at least 2 mm, at least 3 mm, at least 4 mm, at least 5 mm, at least 10 mm, at least 15 mm, at least 20 mm, at least 25 mm, at least 30 mm, at least 35 mm, or at least 40 mm. In some embodiments, the polymer film may include more than one formed shape. In some embodiments, the more than one formed shapes may have the same dimensions, e.g., radius, while in some embodiments the more than one formed shapes may have different dimensions. For example, one formed shape could be a first bend having a radius of 2.5 mm parallel to a second bend having a radius of 5 mm.

In some embodiments, the polymer film may include a notch formed through the polymer film adjacent the bend, such that the notch is aligned with a channel. In some embodiments, a notch may be present in the polymer film in the absence of a formed bend. In some embodiments, the polymer film may have more than one notch. In some embodiments, a notch may have dimensions of 0.3 cm×0.3 cm, 0.6 cm×0.6 cm, 1.2 cm×1.2 cm, or 1.8 cm×1.8 cm on a 3.5 cm×5 cm or a 5 cm×6 cm polymer film. In some embodiments, the notch area is less than 50%, less than 45%, less than 40%, less than 35%, less than 30%, less than 25%, less than 20%, less than 15%, less than 10%, or less than 5% of the total area of the polymer film before the notch is created.

Adhesives

In one aspect, suitable adhesive for use in medical article securement systems of the present disclosure include adhesive that provides acceptable adhesion to and is appropriate for use on human skin (e.g., the adhesive should preferably be non-irritating and non-sensitizing), referred to herein as "skin-contact adhesive". Preferred skin-contact adhesives are commonly pressure sensitive, capable of securely but releasably adhering or bonding to skin (e.g., mammalian skin), and in certain embodiments, preferably have a relatively high moisture vapor transmission rate to allow for moisture evaporation. Suitable pressure-sensitive adhesives include those based on acrylates, polyurethanes, KRATON, and other block copolymers, silicones, rubber based adhesives such as, for example, natural rubber, polyisoprene, polyisobutylene, and butyl rubber, as well as combinations of these adhesives. The pressure-sensitive adhesive may contain tackifiers, plasticizers, rheology modifiers as well as active components including, for example an antimicrobial agent. The pressure-sensitive adhesives that may preferably be used in the medical article securement systems of the present disclosure may include adhesives that are typically applied to the skin such as the acrylate copolymers described in U.S. Pat. No. RE 24,906, the terpolymer described in U.S. Pat. No. 4,737,410, and adhesives described in U.S. Pat. Nos. 3,389,827; 4,112,213; 4,310,509; and 4,323,557. Inclusion of medicaments or antimicrobial agents in the adhesive is also contemplated, as described in U.S. Pat. Nos. 4,310, 509 and 4,323,557 and incorporated herein by reference in their entireties.

In another aspect, suitable adhesive for use in medical article securement systems of the present disclosure may include adhesive that provides acceptable adhesion to a surface other than skin, e.g., a medical article or a portion of the medical article securement system, referred to herein as "contact adhesive". Contact adhesives accommodating various bonding requirements are known in the art and contact adhesives known to those of ordinary skill in the art can be employed in the systems of the present disclosure. In some embodiments, more than one type of adhesive, such as, for example, a skin-contact adhesive, a contact adhesive, or combinations thereof, may be used in medical article securement systems of the present disclosure.

Medical Article Securement Devices

Figure 1:
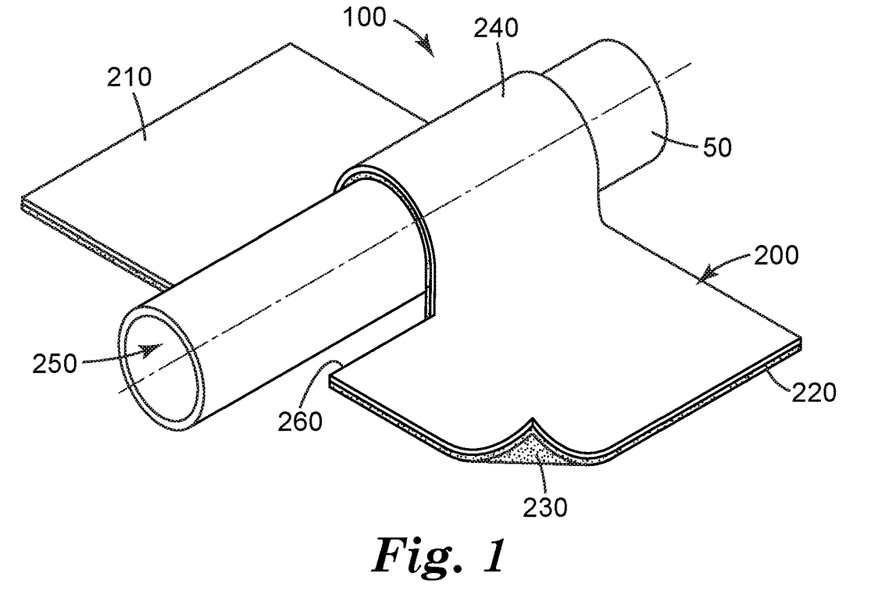
FIG. 1 is a front perspective view of an embodiment of a viscoelastic securement system according to one embodiment of the present disclosure, showing a medical article coupled to a viscoelastic securement device.
Figure 2:
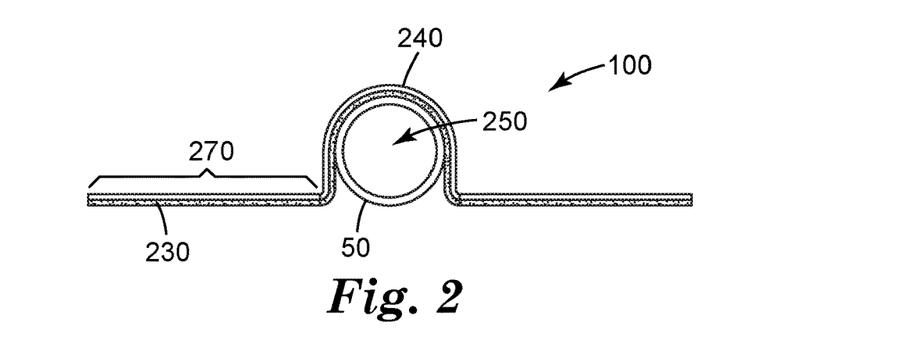
FIG. 2 is a front elevational view of the viscoelastic securement system of FIG. 1.

Medical article securement devices of the present disclosure may be prepared by obtaining a polymer film as described above and coating at least a portion of one face of the polymer film with an adhesive. FIGS. 1 and 2 illustrate a medical article securement device 100 according to one embodiment of the present disclosure. FIG. 1 illustrates a securement device 100 coupled to an exemplary medical article 50. By way of example only, the medical article 50 is illustrated as being a length of tubing. FIG. 2 shows a front elevational view of the securement device 100 and coupled medical article 50 of FIG. 1. The securement device 100 comprises a polymer film 200, the polymer film 200 having a first major surface 210 (e.g., an upper surface) configured to face away from a patient's skin, and a second major surface 220 (e.g., a lower surface) opposite the first major surface 210 that comprises a skin-contact adhesive 230.

As shown in FIGS. 1 and 2, the securement device 100 may include a bend 240 defining a channel 250 dimensioned to receive at least a portion of the medical article 50, and a notch 260 formed through the polymer film 200 adjacent the bend 240, such that the notch 260 is aligned with the channel 250. In some embodiments, the securement device 100 includes at least one flat portion 270 of the polymer film 200 adjacent the bend 240 and the notch 260. As shown in FIGS. 1 and 2, in some embodiments the bend 240 defining the channel 250 and the notch 260 are located between two flat portions 270 of the polymer film 200. The notch 260 is illustrated as being a rectangular portion excised from the polymer film 200, but it could be of other suitable configurations such as, for example square, triangular, circular, or elliptical. In some embodiments, the securement device 100 may include more than one bend 240 defining a channel 250 dimensioned to receive at least a portion of a medical article 50. In some embodiments, the securement device 100 may include more than one notch 260, where the notches 260 may be aligned with a corresponding channel 250 or may be located in a position that is not aligned with a channel 250.

Figure 3:
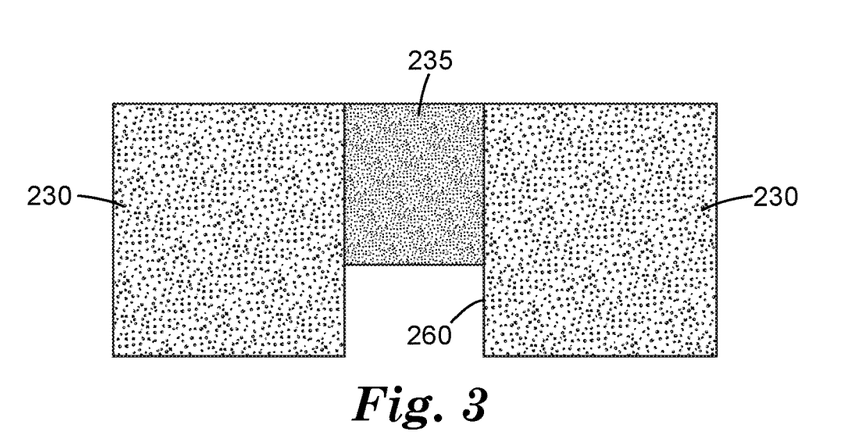
FIG. 3 shows a bottom plan view of a viscoelastic securement device according to another embodiment of the present disclosure.

Referring to FIG. 3, in some embodiments, portions of the second major surface 220 of the polymer film 200 may be partially or fully coated with one or more skin-contact adhesives 230 and one or more contact adhesives 235.

Figure 4:
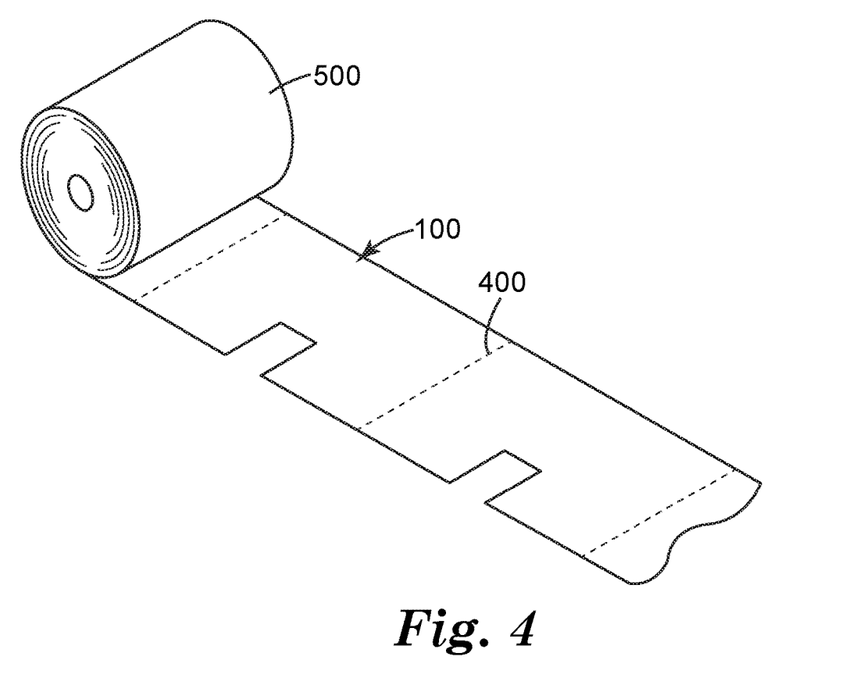
FIG. 4 is a front perspective view of a viscoelastic securement device according to another embodiment of the present disclosure.

In some embodiments, and as shown in FIG. 4, the medical article securement device 100 may be fabricated such that it may form a roll 500 for storage and comprise perforations 400 that allow for individual securement devices 100 to be separated from the roll 500 for use.

In some embodiments, the bend 240 defining a channel 250 may form as the securement device 100 is affixed to the medical article 50. In some embodiments, the bend 240 defining a channel 250 may be formed before the securement device 100 is affixed to the medical article 50. In some embodiments, the bend 240 and channel 250 are dimensioned to accommodate a particular medical article 50 or portion of a medical article 50 (see FIGS. 1 and 5).

Figure 5:
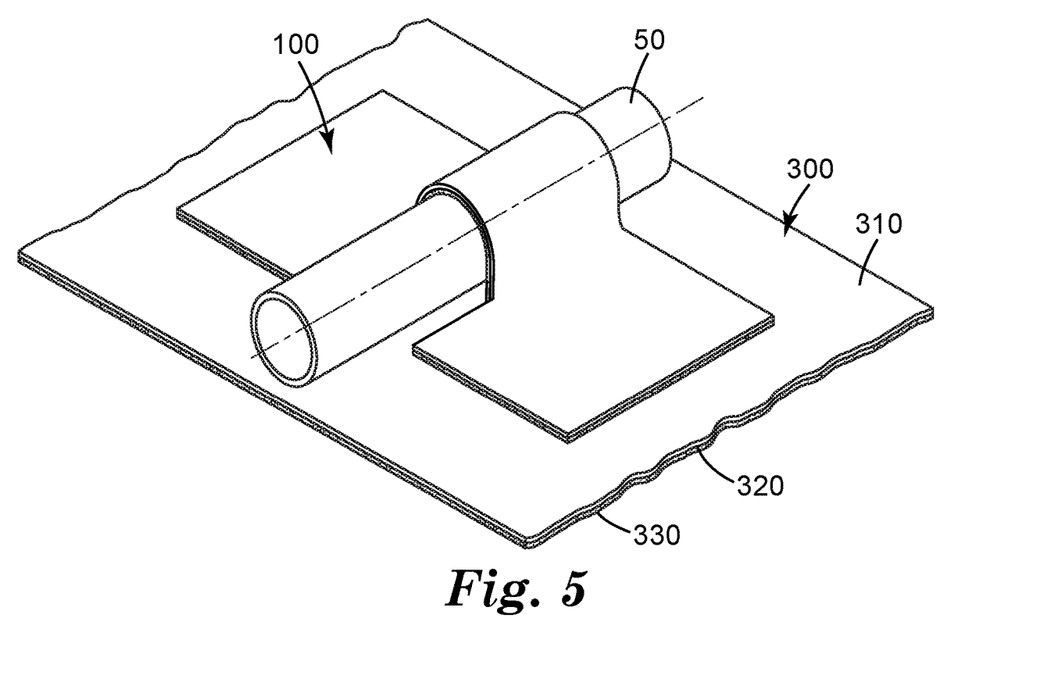
FIG. 5 is a front perspective view of an embodiment of a viscoelastic securement system according to another embodiment of the present disclosure, showing a medical article coupled to a viscoelastic securement system, the viscoelastic securement system comprising a viscoelastic securement device and a base layer.

As shown in FIG. 5, the securement device 100 may comprise a base layer 300 having a first major surface 310 and a second major surface 320 opposite the first major surface 310. The polymer film 200 (e.g., the second major surface 220 of the polymer film 200) can be coupled to the base layer 300 using a variety of coupling means including, but not limited to, one or more of adhesives, cohesives, magnets, welding (e.g., sonic [e.g., ultrasonic] welding), any thermal bonding or heat sealing technique (e.g., heat and/or pressure applied to one or both of the components to be coupled), other suitable coupling means, or combinations thereof. In some embodiments contact adhesive 235 on at least a portion of the second major surface 220 of the polymer film 200 is adhered to the first major surface 310 of the base layer. The base layer 300 first major surface 310 is configured to face away from the patient's skin while the base layer 300 second major surface 320 is configured to face toward the patient's skin and adhere thereto. In some embodiments, the base layer 300 second major surface 320 may comprise a skin-contact adhesive 330 for adhering to the skin. Although only a single shape of the base layer 300 is illustrated, it should be understood that the base layer 300 can take on a variety of shapes and sizes, depending on the shapes and configurations of the other elements of the medical article securement device 100 and the medical article 50 to be coupled to the medical article securement device 100. In some embodiments, the base layer 300 comprises a laminated structure comprising one or more of a fabric, a woven fibrous web, a nonwoven fibrous web, a knit, a polymeric film, or combinations thereof. In some embodiments, the base layer may comprise a commercially available dressing configured to adhere to human skin, such as, for example, TEGADERM Flat Film Dressing, available from 3M Company, St. Paul, Minn., USA.

In some embodiments, the base layer 300 and the skin-contact adhesive 330 can be perforated to provide openings from the first major surface 310 of the base layer 300 all the way through the second major surface 320 and the skin-contact adhesive 330, which can enhance permeability of the base layer 300 and can minimize moisture build-up at the skin surface underlying the base layer 300.

In some embodiments, the securement device 100 may further include one or more release liners (not shown) that can provide a release layer or surface to the skin-contact adhesive 230, 330 or to the contact adhesive 235 prior to use of the securement device 100. Examples of liners suitable for use with systems of the present disclosure can include, but are not limited to, kraft papers, polyethylene, polypropylene, polyester, or combinations thereof. Such liners can be coated with release agents, such as fluorochemicals, silicones, or other suitable low surface energy materials. Other adhesives and release liner combinations known to those of ordinary skill in the art can be employed in the systems of the present disclosure.

Methods of Coupling a Medical Article to a Medical Article Securement System

FIGS. 1 and 5 illustrate methods of coupling various medical articles to medical article securement devices 100 of FIGS. 1-5. Different coupling methods can be used for different systems, and the methods illustrated in FIGS. 1 and 5 are included merely for illustration purposes.

As shown in FIGS. 1 and 5, when a medical article 50 is coupled to the securement device 100, a portion thereof is positioned in a channel 250 defined by a bend 240 and a portion passes through a notch 260 formed through the polymer film 200 adjacent the bend 240, thus inhibiting movement of the medical article 50 in at least a direction that is generally normal to the first major surface 210 of the polymer film 200, i.e., to inhibit the medical article 50 from being pulled away from a patient's skin, as well as movement of the medical article 50 in other directions (e.g., lateral, oblique).

SELECT EMBODIMENTS OF THE PRESENT DISCLOSURE

1. A securement device comprising:
a polymer film having a first major surface and a second major surface opposite the first major surface, the polymer film comprising:
a thickness of at least 0.1 mm,
a glass transition temperature, Tg, of at least 15° C. and no greater than 45° C.,
a tan δ max of at least 0.4, and
a tensile storage modulus E' of at least 10 MPa at 30° C., 1 Hz when tested according to Dynamic Mechanical Analysis; and
an adhesive on the second major surface of the polymer film.
2. The securement device of embodiment 1, wherein the polymer film comprises a polymer selected from the group consisting of a polyurethane, a polyvinyl chloride, an acrylic, a polyester, a polyamide, and combinations thereof.
3. The securement device of embodiment 2, wherein the polyurethane is selected from the group consisting of an ester-based aliphatic polyurethane, an ether-based aliphatic polyurethane, an ester-based aromatic polyurethane, an ether-based aromatic polyurethane, a polycarbonate-based polyurethane, and combinations thereof.
4. The securement device of any of embodiments 1-3, wherein the polymer film has a thickness of at least about 0.3 mm.
5. The securement device of any of embodiments 1-4, wherein the glass transition temperature, Tg, is at least 20° C.
6. The securement device of any of embodiments 1-5, wherein the tan δ max is no greater than 2.0.
7. The securement device of any of embodiments 1-6, wherein the tensile storage modulus E' is at most 2000 MPa at 30° C., 1 Hz when tested according to Dynamic Mechanical Analysis.
8. The securement device of any of embodiments 1-7, wherein the adhesive comprises a skin-contact adhesive.
9. The securement device of any of embodiments 1-8, wherein the securement device has a peak load of at least 15N when tested according to Adhesive Test Method.
10. The securement device any of embodiments 1-9, wherein the polymer film is configured to include a channel dimensioned to receive at least a portion of a medical tubing.
11. The securement device of embodiment 10, wherein the channel is located adjacent at least one flat portion of the polymer film.
12. The securement device of embodiment 10 or 11, wherein the channel is located between two flat portions of the polymer film.
13. The securement device of any of embodiments 10-12, further comprising a notch in the polymer film positioned such that the notch is aligned with the channel.
14. The securement device of embodiment 13, wherein the notch is dimensioned to receive at least a portion of a medical tubing such that the tubing can pass from the second major surface of the backing through the first major surface of the backing.
15. The securement device of any of embodiments 1-14, wherein the first major surface of the polymer film includes a surface modification.
16. The securement device of any of embodiments 1-15, further comprising a base layer having a first major surface and a second major surface opposite the first major surface, wherein the adhesive on the second major surface of the polymer film is adhered to a first major surface of the base layer, and wherein the second major surface of the base layer comprises a skin-contact adhesive.
17. A medical tubing securement device comprising:
a polymer film comprising:
a first major surface,
a second major surface opposite the first major surface,
a formed bend, the bend defining a channel dimensioned to receive at least a portion of a medical tubing, and
a notch formed through the polymer film adjacent the bend, such that the notch is aligned with the channel; and
an adhesive on the second major surface of the polymer film.
18. The medical tubing securement device of embodiment 17, further comprising at least one flat portion of the polymer film adjacent the bend and the notch.
19. The medical tubing securement device of embodiment 18, wherein the bend and the notch are located between two flat portions of the polymer film.
20. The medical tubing securement device of any of embodiments 17-19, wherein the first major surface of the polymer film includes a surface modification.
21. The medical tubing securement device of any of embodiments 17-20, wherein the adhesive is a skin-contact adhesive.
22. The medical tubing securement device of any of embodiments 17-21, further comprising a base layer, wherein the adhesive is adhered to the base layer, and wherein the base layer includes a skin-contact adhesive.
23. A method of securing a medical device, the method comprising:
securing a medical device to the skin of a patient with the securement device of any one of embodiments 1-22.

Objects and advantages of this disclosure are further illustrated by the following non-limiting examples, but the particular materials and amounts thereof recited in these examples, as well as other conditions and details, should not be construed to unduly limit this disclosure.

EXAMPLES

Unless otherwise noted, all parts, percentages, ratios, etc. in the Examples and the rest of the specification are by weight.

TABLE 1

Materials

| Material | Description | Source |
|---|---|---|
| DIARY MM3520 | Polyether-based viscoelastic thermoplastic polyurethane | SMP Technologies, Tokyo, Japan |
| FOMREZ 44-111 | Poly(butylene adipate) polyol with an Mn of 1000 g/mol | Chemtura Corporation, Middlebury, CT |

TABLE 1-continued

Materials

| Material | Description | Source |
| --- | --- | --- |
| 1,4-Butanediol | 1,4-Butanediol | Ashland, Inc, Covington, KY |
| Glycerol | Ultrapure HPLC grade, #38988 | Alfa Aesar, Ward Hill, MA |
| BICAT 8 | Bismuth and Zinc Carboxylate | Shepherd Chemical Company, Norwood, OH |
| DESMODUR-W | Bis(4-isocyanatocyclohexyl) methane | Bayer MaterialScience, Pittsburgh, PA |
| MONDUR MLQ | Monomeric diphenylmethane diisocyanate with high 2,4'-isomer content | Bayer MaterialScience, Pittsburgh, PA |
| DESMODUR N3300 | HDI-based multifunctional isocyanate | Bayer MaterialScience, Pittsburgh, PA |
| TERATHANE PTMEG 650 | Polyether glycol with an Mn of 650 g/mol; Product No. 345288 | Sigma Aldrich, St. Louis, MO |
| CAPA 3031 | Polycaprolactone triol with an Mn of 300 g/mol | Perstorp, Malmo, Sweden |
| K-188 | Aliphatic polyester diol with an Mn of 488 g/mol | King Industries, Norwalk, CT |
| Acrylic Adhesive Tape | 0.03 mm thick acrylic transfer tape for skin contact | 3M, St. Paul, MN |
| 467MP Transfer Tape | 3M High Performance Adhesive Transfer Tape 467MP, 0.06 mm thick acrylic transfer tape | 3M, St. Paul, MN |
| PVC tubing | PVC tubing with an outside diameter of 0.25" (0.6 cm) and an inside diameter of 0.13" (0.3 cm). Product Number 14-169-7A | Fisher Scientific, Waltham, MA |
| ABS Plate | Acrylonitrile-butadiene-styrene polymer 11 cm long, 5 to 8 cm wide, and 0.3 cm thick | Plastics International, Eden Prairie, MN |
| TEGADERM 1624W | 3M TEGADERM Transparent Film Dressing Frame Style 1624W, 2⅜ inch × 2¾ inch (6 cm × 7 cm) | 3M, St. Paul, MN |
| CXBI061 | Bismuth neodecanoate | Gelest Inc., Morrisville, PA |
| Dibutylin dilaurate | Di-n-butyltin dilaurate, (95%) product #71130 | Alfa Aesar, Ward Hill, MA |
| Polyester tape | Polyester tape with silicone adhesive; Product No. 8403 | 3M, St. Paul, MN |
| GENIOMER 200 | Thermoplastic silicone elastomer | Wacker Chemie, Munich, Germany |
| ST-3655 | 87 Shore A thermoplastic polyurethane | Argotec, Greenfield, MA |
| PET | Polyethylene terephthalate film, 2 mils (51 micrometer) thick | 3M, St. Paul, MN |
| Tape Primer 94 | Liquid used to promote adhesion of 3M tapes to surfaces | 3M, St. Paul, MN |
| Silicone Adhesive | Q2-7735 Adhesive | Dow Corning, Midland, MI |

Adhesive Test Method

PVC tubing was secured to an ABS plastic plate using the securement device Example materials. The ABS plate was mounted in a 90° Peel Test Apparatus in an INSTRON load frame (Instron Industrial Products, Norwood, Mass., USA), and the end of the tubing was secured in the top grip of the load frame. The sample was tested to determine the failure mode at a displacement rate of 20 in/min (50.8 cm/min). Unless otherwise specified, two replicates were performed, and the average peak load is reported.

Dynamic Mechanical Analysis ("DMA") Test Method

Example films were cut into strips 6.2 mm wide and about 4 cm long. The thickness of each film was measured. The films were mounted in the tensile grips of a Q800 DMA (TA Instruments, New Castle, Del., USA) with an initial grip separation between 17 mm and 19 mm. The samples were then tested at an oscillation of 0.2% strain and 1 Hz throughout a temperature ramp from at least −20° C. to 150° C. at a rate of 2° C. per minute. The temperature at which the tan delta signal reached a maximum was recorded as the glass transition temperature.

Preparatory Example 1

Pellets of DiARY MM3520 were extruded with a single screw extruder into films 20 cm wide and 0.6 mm thick or 0.3 mm thick.

Preparatory Example 2

An ester-based aliphatic polyurethane film was prepared by reactive extrusion. The film was formed from a mixture of FOMREZ 44-111 (45.2 wt %), 1,4-butanediol (10.4 wt %), glycerol (0.3%), BICAT 8 (0.1%), and DESMODUR-W (43.9 wt %) and was 0.13 mm thick.

Preparatory Example 3

An ester-based aliphatic polyurethane film was prepared with the same method as Preparatory Example 2, except the film was 0.05 mm thick.

Preparatory Example 4

An ether-based aliphatic polyurethane was prepared by reactive compounding of a mixture of Terathane 650 (46.0 wt %), 1,4-butanediol (8.8 wt %), and CAPA 3031 (0.4%), bismuth neodecanoate (0.3%), and DESMODUR-W (44.5 wt %) and was 0.13 mm thick. The reactive mixtures were mixed for at least five minutes at 170° C. to allow polymerization to occur. Films were then pressed with a hydraulic press at 160° C. to give a thicknesses of 0.3 mm.

Preparatory Example 5

A thermosetting ester-based aliphatic polyurethane was prepared by mixing a polyester diol (K-188, 61 wt %), a multifunctional HDI-based isocyanate (DESMODUR N3300, 39 wt %), and dibutyltin dilaurate (0.1 wt %). This mixture was then coated between polyester liners to a thickness of 0.6 mm and allowed to fully cure in an oven at 70° C.

Preparatory Examples 6 and 10-18

A series of ten polyurethanes were prepared by reactive compounding of a mixture of FOMREZ 44-111, 1,4-butanediol, and MONDUR MLQ in the ratios shown in Table 4. The reactive mixtures were mixed for at least five minutes at 195° C. to allow polymerization to occur. Films were then pressed with a hydraulic press at 160° C. to give the thicknesses shown in Table 4.

Preparatory Examples 7-9

A series of three viscoelastic crosslinked polyurethane films were prepared by reactive extrusion. The films were formed from a mixture of FOMREZ 44-111, 1,4-butanediol, and MONDUR MLQ in the ratios shown in Table 4. The film thicknesses are shown in Table 4.

Preparatory Example 19

A sheet of viscoelastic polyurethane was prepared by pressing pellets of DiARY MM3520 in a Model 2699 hydraulic press (Carver, Inc., Wabash, Ind., USA) at 323° F. (162° C.) with force of 20,000 lbf (89,000 N) for 30 minutes using 1 mm thick wooden shims. The sheet was then placed on an embossing tool comprising a steel plate with an array of machined posts. Each post was 0.6 mm tall with a square base 0.2 mm×0.2 mm and a square tip 0.1 mm×0.1 mm, and they were positioned in an array having square packing and a pitch of 0.3 mm. The viscoelastic urethane sheet and the embossing tool were placed in the hydraulic press at a temperature of 323° F. (162° C.) with force of 20,000 lbf (89,000 N) for 5.5 minutes. After cooling, the viscoelastic urethane sheet was removed from the embossing tool to provide an embossed sheet with cavities on one surface matching the dimensions on the posts on the tool. The thickness of the sheet was 1 mm. This embossed sheet was folded around a stainless steel tube with a diameter of 5 mm with the embossed pattern toward the outside of the fold, and the assembly was heated in an oven at 130° C. for 20 minutes to form a fold in the embossed sheet with the same radius as the tube. With stainless steel tube still in place, each of the two ends of this assembly was folded back approximately 90 degrees and taped to a glass jar (6 cm diameter). As a result, the two outside portions of the sheet followed the contour of the glass jar, and the center of the sheet was folded around the stainless steel tube. This assembly was heated in a 130° C. oven. After cooling, acrylic adhesive tape was laminated to the surface of the sheet that was not embossed. The resulting laminate was found to conform well to a flexible tube.

Example 1: 0.3 mm Formed Film with Notched Edge

A piece of 0.3 mm thick film from Preparatory Example 1 was cut to a 5 cm×6 cm dimension. The center section of the sheet parallel to the 5 cm edge was masked with a piece of polyester tape. The sheet was then folded generally 180° around a cylindrical wooden applicator stick with a diameter of 2 mm with the polyester tape backing contacting the wood. The fold was secured with binder clips, and the remaining flaps of the polymer sheet were taped down to a steel plate with polyester tape. This form was heat-set in a 125° C. oven for 30 minutes. After cooling, the sheet retained a form with a center loop of polymer protruding approximately 0.7 cm above the surface of the rest of the polymer sheet. The polyester tape was removed. A 1.2 cm×1.2 cm section of the formed sheet was removed from the center of one of the 6 cm edges to create a "notch." Acrylic adhesive tape was laminated to the inner face of the formed sheet, and the laminate was used to secure PVC tubing to an ABS plate to form a notched construction, as shown in FIG. 1. The assembly was tested with the Adhesive Test Method with the tubing being pulled from notched edge of the film.

Example 2: 0.3 mm Formed Film

A construction equivalent to that in Example 1 was prepared except the 1.2 cm×1.2 cm section of the laminate was not removed. The laminate was used to secure PVC tubing to an ABS plate and the assembly was tested with the Adhesive Test Method.

Example 3: 0.6 mm Formed Film

A construction equivalent to that in Example 2 was prepared and tested except that the extruded film was a 0.6 mm thick film from Preparatory Example 1.

Example 4: Crosslinked Film with Notched Edge

A piece of film from Preparatory Example 2 was cut to 5 cm×6 cm. A 1.2 cm×1.2 cm section of the laminate was removed from the center of one of the 6 cm edges. Acrylic adhesive tape was laminated to one face of the sheet, and the laminate was used to secure PVC tubing to an ABS plate to form a construction similar to that shown in FIG. 1 by wrapping the laminate around the tubing as it was adhered to the ABS plate. The assembly was tested with the Adhesive Test Method with the tubing being pulled from notched edge of the film.

Example 5: Crosslinked Film

A construction equivalent to that in Example 4 was prepared and tested except the 1.2 cm×1.2 cm section of the laminate was not removed.

Example 6: Formed Film with Notched Edge Over Flat Film

A piece of 0.3 mm thick film from Preparatory Example 1 was cut to 5 cm×3.5 cm. The center section of the sheet parallel to the 5 cm edge was masked with a piece of polyester tape. The sheet was then folded generally 180° around a wooden applicator stick with a diameter of 2 mm with the tape contacting the wood. The fold was secured with binder clips, and the remaining flaps of the polymer sheet were taped down to a steel plate with polyester tape. This form was heat-set in a 125° C. oven for 30 minutes. The polyester tape was removed. A 1.2 cm×1.2 cm section of the formed sheet was removed from the center of one of the 3.5 cm edges. A piece of 467MP Transfer Tape was laminated to the inner face of the formed sheet. A TEGADERM Dressing (6 cm×7 cm) was applied to an ABS plate, and the surface of the TEGADERM Dressing was wiped with Tape Primer 94. The formed film was then used to secure PVC tubing to the top of the TEGADERM Dressing to form a construction as shown in FIG. 5. The assembly was tested with the Adhesive Test Method with the tubing being pulled from notched edge of the film.

Example 7: Formed Film with Notched Edge Over Flat Film

A piece of film from Preparatory Example 2 was cut to 5 cm by 3.5 cm. A 1.2 cm×1.2 cm section of the laminate was removed from the center of one of the 3.5 cm edges. A piece of 467MP Transfer Tape was laminated to one face of the film. A TEGADERM Dressing (6 cm×7 cm) was applied to an ABS plate, and the surface of the TEGADERM Dressing was wiped with Tape Primer 94. The viscoelastic laminate was then used to secure PVC tubing to the top of the TEGADERM Dressing to form a construction as shown in FIG. 5 by wrapping the laminate around the tubing as it was adhered to the TEGADERM dressing. The assembly was tested with the Adhesive Test Method with the tubing being pulled from notched edge of the film.

Example 8: Silicone Adhesive on 0.3 mm Film with Notch

A piece of 0.3 mm thick film from Preparatory Example 1 was coated with Silicone Adhesive solution (as received) under a knife coater with a 0.1 mm gap. The coating was dried in 70° C. oven for 10 minutes. A piece of this coated film was cut to 5 cm×3.5 cm. A 1.2 cm×1.2 cm section of the laminate was removed from the center of one of the 3.5 cm edges. A TEGADERM Dressing (6 cm×7 cm) was applied to an ABS plate. The coated film was then used to secure PVC tubing to the top of the TEGADERM Dressing to form a construction as shown in FIG. 5. The assembly was tested with the Adhesive Test Method with the tubing being pulled from notched edge of the film.

Example 9: 0.13 mm Film

A piece of 0.3 mm thick film from Preparatory Example 1 was compressed in a hydraulic press to produce a film 0.13 mm thick. A piece of this thinner film was cut to 5 cm by 6 cm. A 1.2 cm×1.2 cm section of the laminate was removed from the center of one of the 6 cm edges. Acrylic adhesive tape was laminated to one face of the sheet, and the laminate was used to secure PVC tubing to an ABS plate to form a construction similar that shown in FIG. 1 by wrapping the laminate around the tubing as it was adhered to the ABS plate. The assembly was tested with the Adhesive Test Method with the tubing being pulled from notched edge of the film.

Example 10: Ether-Based Aliphatic Urethane

A piece of 0.3 mm thick film from Preparatory Example 4 was cut to 5 cm×6 cm. A 1.2 cm×1.2 cm section of the laminate was removed from the center of one of the 6 cm edges. Acrylic adhesive tape was laminated to one face of the sheet, and the laminate was used to secure PVC tubing to an ABS plate to form a construction similar to that shown in FIG. 1 by wrapping the laminate around the tubing as it was adhered to the ABS plate. The assembly was tested with the Adhesive Test Method with the tubing being pulled from notched edge of the film.

Example 11: Thermosetting Ester-Based Aliphatic Urethane

A piece of 0.6 mm thick film from Preparatory Example 5 was cut to 5 cm×6 cm. A 1.2 cm×1.2 cm section of the laminate was removed from the center of one of the 6 cm edges. Acrylic adhesive tape was laminated to one face of the sheet, and the laminate was used to secure PVC tubing to an ABS plate to form a construction similar to FIG. 1 by wrapping the laminate around the tubing as it was adhered to the ABS plate. The assembly was tested with the Adhesive Test Method with the tubing being pulled from notched edge of the film.

Comparative Example 1: Elastomer

A film of GENIOMER 200 was compression molded to a thickness of 0.3 mm in a hydraulic press at 170° C. This film was then formed and tested as in Example 1.

Comparative Example 2: Elastomer

A construction equivalent to that in Example 1 was prepared and tested except the film was a 0.3 mm thick sample of ST-3655.

Comparative Example 3: PET Film

A construction equivalent to that in Example 4 was prepared and tested except the film was a 0.05 mm thick PET film.

Comparative Example 4: TEGADERM Dressing with Notched Configuration

A TEGADERM flat film dressing was first cut into a strip 5 cm wide; additionally a 1.2 cm×1.2 cm square notch was cut from one long edge of the dressing. This modified dressing was then used to secure PVC tubing to an ABS plate with the notch placed over the tubing, such that only a 3.8 cm length of the tubing was covered by the film. The ends of the dressing were then trimmed to leave a 5 cm by 5 cm area, which was again, centered around the tubing. The assembly was tested with the Adhesive Test Method.

Comparative Example 5: TEGADERM Dressing (without Notch)

A TEGADERM flat film dressing was first cut into a strip 5 cm wide, which was then used to secure PVC tubing to an ABS plate. The ends of the dressing were then trimmed to leave a 5 cm by 5 cm area of material, with the tubing centered underneath. The assembly was tested with the Adhesive Test Method and gave a peak load of 16.5 N.

Comparative Example 6: 0.05 mm Film

A piece of 0.3 mm thick film from Preparatory Example 1 was compressed in a hydraulic press to produce a film 0.05 mm thick. A piece of this thinner film was cut to 5 cm×6 cm. A 1.2 cm×1.2 cm section of the laminate was removed from the center of one of the 6 cm edges. Acrylic adhesive tape was laminated to one face of the sheet, and the laminate was used to secure PVC tubing to an ABS plate to form a construction similar to that shown in FIG. 1 by wrapping the laminate around the tubing as it was adhered to the ABS plate. The assembly was tested with the Adhesive Test Method with the tubing being pulled from notched edge of the film.

Comparative Example 7: 0.05 mm Crosslinked Film

A piece of 0.05 mm thick film from Preparatory Example 3 was cut to 5 cm×6 cm. A 1.2 cm×1.2 cm section of the laminate was removed from the center of one of the 6 cm edges. Acrylic adhesive tape was laminated to one face of the sheet, and the laminate was used to secure PVC tubing to an ABS plate to form a construction similar to that shown in FIG. 1 by wrapping the laminate around the tubing as it was adhered to the ABS plate. The assembly was tested with the Adhesive Test Method with the tubing being pulled from notched edge of the film.

Figure 6:
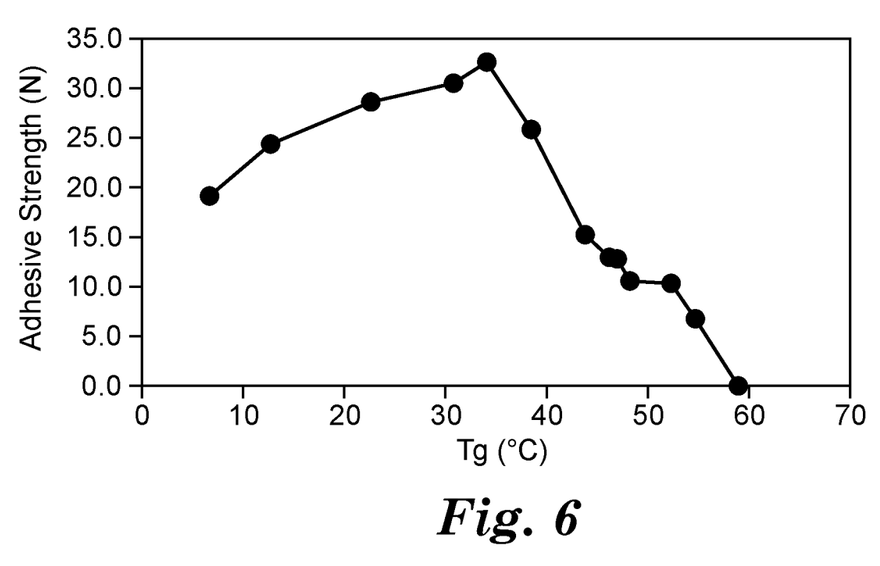
FIG. 6 is a graph of adhesive strength (N) against glass transition temperature (Tg) of various polymers.

Examples 12-16 and Comparative Examples 8-15: Formed Film with Notched Configuration Pieces of film from Preparatory Examples 4 through Preparatory Example 16 were each cut to 3 cm×6 cm. The center section of the sheets parallel to the 3 cm edge were masked with polyester tape. The sheets were then folded generally 180° around cylindrical wooden applicator sticks with a diameter of 2 mm with the tape contacting the wood. The folds were secured with binder clips, and the remaining flaps of the polymer sheets were taped down to a steel plate with polyester tape. This form was heat-set in a 125° C. oven for 30 minutes. After cooling, the sheets retained a form with a center loop of polymer protruding above the surface of the rest of the polymer sheet. The polyester tape was removed. A 1.0 cm×1.0 cm section of each sheet was removed from the center of one of the 6 cm edges. Acrylic adhesive tape was laminated to the inner face of the formed sheets, and the laminate was used to secure PVC tubing to an ABS plate to form a construction as shown in FIG. 1. The assembly was tested with the Adhesive Test Method with the tubing being pulled from notched edge of the film. Three replicates were tested for each example, and the average result is shown in Table 4 and FIG. 6. As the data in Table 4 and FIG. 6 show, there is an unexpected correlation between the Tg of a polymer film and the polymer film's adhesive performance. Surprisingly, adhesive performance reaches a maximum when the polymer film has a Tg within an optimal range, i.e., about 15° C. to about 45° C. If the polymer film is too stiff, i.e., Tg is greater than about 45° C., the polymer film will not conform to the skin, resulting in a low adhesive strength. On the other hand, if the polymer film is too soft, i.e., Tg is less than about 15°, the polymer film may readily shear off of the skin when a force is applied. The data in FIG. 6 show that the viscoelastic properties of a polymer film can be tuned into a specific range to create a medical securement device with desirable adhesive characteristics.

Examples 1, 4, 10 and 11 and Comparative Examples 1, 2, 3, and 4 all have similar shapes and areas. These Examples were tested with the DMA Test Method and the Adhesive Test Method, and the results are shown in Table 2.

TABLE 2

Constructions with Varied Materials Properties - All Notched

| Example | Material | Thickness (mm) | DMA Test Method | | | Adhesive Test Method | |
|---|---|---|---|---|---|---|---|
| | | | Tg (° C.) | tan delta max. | E' at 30° C., 1 Hz (MPa) | Peak Load (N) | Failure Mode |
| EX. 1 | Prep. Ex. 1 | 0.3 | 42.0 | 0.70 | 1641 | 36.0 | Adhesive failure |
| EX. 4 | Prep. Ex. 2 | 0.13 | 43.9 | 1.33 | 235 | 28.9 | Adhesive failure |
| EX. 10 | Prep. Ex. 4 | 0.3 | 38.5 | 0.83 | 85.7 | 36.0 | Adhesive Failure |
| EX. 11 | Prep. Ex. 5 | 0.6 | 29.0 | 1.69 | 22.3 | 35.9 | Adhesive Failure |
| Comp. Ex. 1 | GENIOMER 200 | 0.3 | 53.3 | 0.10 | 5.6 | 4.0 | Adhesive failure |
| Comp. Ex. 2 | ST-3655 | 0.3 | −14.2 | 0.29 | 32 | 12.0 | Adhesive failure |
| Comp. Ex. 3 | PET Film | 0.05 | 111.7 | 0.15 | 5125 | 28.0 | Film tear to release tubing |
| Comp. Ex. 4 | TEGADERM Film | 0.02 | — | — | — | 8.9 | Film tear to release tubing |

The data in Table 2 show the performance of constructions using polymer films that have the claimed viscoelastic properties (i.e., Examples 1, 4, 10 and 11) as compared to polymer films that do not have the claimed viscoelastic properties (i.e., Comparative Examples 1-4). As the data show, polymer films prepared according to the present disclosure (i.e., Examples 1, 4, 10 and 11) demonstrate better adhesive performance than the comparative examples (i.e., Comparative Examples 1-4).

Examples 1, 2, 3, 6, 8, 9, and 10 and Comparative Example 1 were all derived from the material of Preparatory Example 1. These Examples were tested with the Adhesive Test Method, and the results are shown in Table 3.

TABLE 3

Comparison of Construction with Prep. Example 1

| | | | | Adhesive Test Method | |
| --- | --- | --- | --- | --- | --- |
| Example | Material | Thickness (mm) | Notch | Peak Load (N) | Failure Mode |
| EX. 1 | Prep. Ex. 1 | 0.3 | Yes | 36.0 | Adhesive failure |
| EX. 2 | Prep. Ex. 1 | 0.3 | No | 17.3 | Adhesive failure |
| EX. 3 | Prep. Ex, 1 | 0.6 | No | 25.8 | Adhesive failure |
| EX. 6 | Prep. Ex. 1 and TEGADERM Film | 0.3 | Yes | 35.6 | Adhesive failure |
| EX. 8 | Prep. Ex. 1, TEGADERM Film, Silicone Adhesive | 0.3 | Yes | 71.6 | Adhesive Failure |
| EX. 9 | Prep. Ex. 1 | 0.13 | Yes | 36.0 | Adhesive Failure |
| Comp. Ex. 6 | Prep. Ex. 1 | 0.05 | Yes | 22.2 | Film tear to release tubing |

The data in Table 3 show the effects of varied device constructions while using the same general materials. The presence of a notch in the sample generally improves performance, and thicker polymer films (i.e., greater than or equal to 0.3 mm) tend to improve performance.

Examples 4 and 5 and Comparative Example 7 were all derived from the same polymer formulation (Preparatory Examples 2 and 3). These Examples were tested with the Adhesive Test Method, and the results are shown in Table 4.

TABLE 4

Comparison of Construction with Prep. Examples 2 and 3

| | | | | Adhesive Test Method | |
| --- | --- | --- | --- | --- | --- |
| Example | Material | Thickness (mm) | Notch | Peak Load (N) | Failure Mode |
| EX. 4 | Prep. Ex. 2 | 0.13 | Yes | 28.9 | Adhesive failure |
| EX. 5 | Prep. Ex. 2 | 0.13 | No | 16.0 | Adhesive failure |
| EX. 7 | Prep. Ex. 2 + TEGADERM 1624W | 0.13 | Yes | 31.1 | Film tear to release tubing |
| Comp. Ex. 7 | Prep. Ex. 3 | 0.05 | Yes | 9.8 | Film tear to release tubing |

The data in Table 4 show the effects of varied device constructions while using the same general materials. As the data show, the notch in the sample generally improves performance, and thicker polymer films tend to help the performance.

Examples 12-16 and Comparative Examples 8-15 all have similar dimensions, but are derived from polymers with systematically varied viscoelastic properties. These Examples were tested with the DMA Test Method and the Adhesive Test Method, and the results are shown in Table 5.

TABLE 5

Performance Variation with Viscoelastic Properties

| Ex. | Material | FOMREZ 44-111 | 1,4-BD | MLQ | Thickness (mm) | Tg (° C.) | tan delta max. | E' at 30° C., 1 Hz (MPa) | Adhesive Test Method Peak Load (N) |
|---|---|---|---|---|---|---|---|---|---|
| Comp. Ex. 8 | Prep. Ex. 6 | 29.0% | 16.7% | 54.3% | 0.6 | 59.0 | 1.18 | 1834 | 0.0 |
| Comp. Ex. 9 | Prep. Ex. 7 | 31.0% | 16.1% | 52.9% | 0.7 | 54.7 | 1.23 | 1657 | 6.7 |
| Comp. Ex. 10 | Prep. Ex. 8 | 33.0% | 15.4% | 51.6% | 0.7 | 52.3 | 1.41 | 1493 | 10.3 |
| Comp. Ex. 11 | Prep. Ex. 9 | 35.0% | 14.8% | 50.2% | 0.6 | 48.2 | 1.37 | 1019 | 10.6 |
| Comp. Ex. 12 | Prep. Ex. 10 | 37.0% | 14.1% | 48.9% | 0.6 | 47.0 | 1.30 | 1202 | 12.8 |
| Comp. Ex. 13 | Prep. Ex. 11 | 39.0% | 13.4% | 47.6% | 0.7 | 46.2 | 1.31 | 506 | 12.9 |
| EX. 12 | Prep. Ex. 12 | 41.0% | 12.8% | 46.2% | 0.6 | 43.8 | 1.28 | 412 | 15.2 |
| EX. 13 | Prep. Ex. 13 | 43.0% | 12.1% | 44.9% | 0.6 | 38.5 | 1.19 | 210 | 25.8 |
| EX. 14 | Prep. Ex. 14 | 45.0% | 11.5% | 43.5% | 0.6 | 34.1 | 1.16 | 67.2 | 32.6 |
| EX. 15 | Prep. Ex. 15 | 47.0% | 10.8% | 42.2% | 0.7 | 30.8 | 0.99 | 56.4 | 30.5 |
| EX. 16 | Prep. Ex. 16 | 51.0% | 9.5% | 39.5% | 0.6 | 22.6 | 1.07 | 14.8 | 28.6 |
| Comp. Ex. 14 | Prep. Ex. 17 | 55.0% | 8.2% | 36.8% | 0.7 | 12.7 | 1.12 | 6.6 | 24.4 |
| Comp. Ex. 15 | Prep. Ex. 18 | 59.0% | 6.9% | 34.1% | 0.6 | 6.7 | 1.13 | 6.1 | 19.1 |

The data in Table 5 show the effects of a single type of construction and single set of raw materials, where the ratios of the materials are systematically varied to span the entire range of viscoelastic properties of interest. Comparative Examples 8-13 are too stiff for optimal performance. Examples 12-16 are in the desired range. Comparative Examples 14 and 15 are too compliant for optimal performance.

All cited references, patents, and patent applications in the above application for letters patent are herein incorporated by reference in their entirety in a consistent manner. In the event of inconsistencies or contradictions between portions of the incorporated references and this application, the information in the preceding description shall control. The preceding description, given in order to enable one of ordinary skill in the art to practice the claimed disclosure, is not to be construed as limiting the scope of the disclosure, which is defined by the claims and all equivalents thereto.

What is claimed is:

1. A securement device comprising:
   a polymer film having a first major surface and a second major surface opposite the first major surface, the polymer film comprising:
   a thickness of at least 0.1 mm,
   a glass transition temperature, Tg, of at least 15° C. and no greater than 45° C.,
   a tan δ max of at least 0.4, and
   a tensile storage modulus E' of at least 10 MPa at 30° C., 1 Hz when tested according to Dynamic Mechanical Analysis;
   an adhesive on the second major surface of the polymer film;
   wherein the polymer film comprises a polymer selected from the group consisting of a polyurethane, a polyvinyl chloride, an acrylic, a polyester, a polyamide, and combinations thereof.

2. The securement device of claim 1, wherein the polyurethane is selected from the group consisting of an ester-based aliphatic polyurethane, an ether-based aliphatic polyurethane, an ester-based aromatic polyurethane, an ether-based aromatic polyurethane, a polycarbonate-based polyurethane, and combinations thereof.

3. The securement device of claim 1, wherein the polymer film has a thickness of at least about 0.3 mm.

4. The securement device of claim 1, wherein the glass transition temperature, Tg, is at least 20° C.

5. The securement device of claim 1, wherein the tan δ max is no greater than 2.0.

6. The securement device of claim 1, wherein the tensile storage modulus E' is at most 2000 MPa at 30° C., 1 Hz when tested according to Dynamic Mechanical Analysis.

7. The securement device of claim 1, wherein the securement device has a peak load of at least 15N when tested according to Adhesive Test Method.

8. The securement device of claim 1, wherein the polymer film is configured to include a channel dimensioned to receive at least a portion of a medical tubing.

9. The securement device of claim 8, wherein the channel is located adjacent at least one flat portion of the polymer film.

10. The securement device of claim 8, wherein the channel is located between two flat portions of the polymer film.

11. The securement device of claim 8, further comprising a notch in the polymer film positioned such that the notch is aligned with the channel.

12. The securement device of claim 11, wherein the notch is dimensioned to receive at least a portion of a medical tubing such that the tubing can pass from the second major surface of a backing through the first major surface of the backing.

13. The securement device of claim 1, wherein the first major surface of the polymer film includes a surface modification.

14. The securement device of claim 1, further comprising a base layer having a first major surface and a second major surface opposite the first major surface, wherein the adhesive on the second major surface of the polymer film is adhered to a first major surface of the base layer, and wherein the second major surface of the base layer comprises a skin-contact adhesive.

* * * * *